US011308645B2

(12) United States Patent
Ehrl et al.

(10) Patent No.: US 11,308,645 B2
(45) Date of Patent: Apr. 19, 2022

(54) APPARATUS AND METHOD FOR WIDE-RANGE OPTICAL TRACKING DURING MEDICAL IMAGING

(71) Applicant: The Board of Trustees of the Leland Stanford Junior University, Palo Alto, CA (US)

(72) Inventors: Jakob Ehrl, Untergriesbach (DE); Julian Maclaren, Menlo Park, CA (US); Murat Aksoy, San Jose, CA (US); Roland Bammer, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 923 days.

(21) Appl. No.: 15/977,900

(22) Filed: May 11, 2018

(65) Prior Publication Data
US 2018/0325415 A1 Nov. 15, 2018

Related U.S. Application Data

(60) Provisional application No. 62/505,751, filed on May 12, 2017.

(51) Int. Cl.
*G06T 7/80* (2017.01)
*G06T 7/73* (2017.01)
(Continued)

(52) U.S. Cl.
CPC .............. *G06T 7/85* (2017.01); *A61B 5/055* (2013.01); *A61B 5/1127* (2013.01); *G01R 33/283* (2013.01); *G01R 33/56509* (2013.01); *G06T 7/246* (2017.01); *G06T 7/73* (2017.01); *A61B 5/721* (2013.01); *G01R 33/385* (2013.01); *G01R 33/5608* (2013.01); *G06T 11/006* (2013.01);
(Continued)

(58) Field of Classification Search
None
See application file for complete search history.

(56) References Cited

U.S. PATENT DOCUMENTS 5,545,993 A 8/1996 Taguchi et al.
5,923,727 A * 7/1999 Navab ................ A61B 6/547
378/207

(Continued)

FOREIGN PATENT DOCUMENTS

WO WO-2005124687 A1 * 12/2005 ............. G06T 7/285

OTHER PUBLICATIONS

Aksoy et al., "A complete neuroimaging protocol with optical prospective motion correction", 2014, Proc. Intl. Soc. Mag. Reson. Med. v22.
Ehrl et al., "A Reliability Measure for Merging Data from Multiple Cameras in Optical Motion Correction", 2014, ISMRM workshop on Motion Correction in MRI, Tromso, Norway.

*Primary Examiner* — Angela M Hoffa
*Assistant Examiner* — Younhee Choi
(74) *Attorney, Agent, or Firm* — Lumen Patent Firm

(57) ABSTRACT

Methods to quantify motion of a human or animal subject during a magnetic resonance imaging (MRI) exam are provided. In particular, these algorithms make it possible to track head motion over an extended range by processing data obtained from multiple cameras. These methods make current motion tracking methods more applicable to a wider patient population.

13 Claims, 9 Drawing Sheets

(51) Int. Cl.
*G01R 33/565* (2006.01)
*G06T 11/00* (2006.01)
*G01R 33/28* (2006.01)
*A61B 5/11* (2006.01)
*G06T 7/246* (2017.01)
*A61B 5/055* (2006.01)
*G01R 33/385* (2006.01)
*G01R 33/56* (2006.01)
*A61B 5/00* (2006.01)

(52) U.S. Cl.
CPC ............... *G06T 2207/10021* (2013.01); *G06T 2207/10088* (2013.01); *G06T 2207/30204* (2013.01)

(56) References Cited

U.S. PATENT DOCUMENTS

| | | | |
|---|---|---|---|
| 8,848,977 B2 | 9/2014 | Bammer et al. | |
| 2005/0054910 A1* | 3/2005 | Tremblay | A61B 5/055 600/411 |
| 2011/0044546 A1 | 2/2011 | Pan et al. | |
| 2012/0121124 A1* | 5/2012 | Bammer | G06T 7/248 382/103 |
| 2013/0114851 A1 | 5/2013 | Foote et al. | |
| 2014/0176599 A1* | 6/2014 | Watanabe | G06K 9/00228 345/619 |
| 2016/0035108 A1* | 2/2016 | Yu | A61B 5/0077 382/131 |

* cited by examiner

Camera 1 only    Camera 1 & 2    Camera 2 only $$\begin{bmatrix} R_{11}^Y x_K^w - & R_{11}^Y y_K^w - & R_{11}^Y z_K^w - & R_{12}^Y x_K^w - & R_{12}^Y y_K^w - & R_{12}^Y z_K^w - & R_{13}^Y x_K^w - & R_{13}^Y y_K^w - & R_{13}^Y z_K^w - & R_{11}^Y - & R_{12}^Y - & R_{13}^Y - \\ R_{31}^Y u_K^{Cy} x_K^w & R_{31}^Y u_K^{Cy} y_K^w & R_{31}^Y u_K^{Cy} z_K^w & R_{32}^Y u_K^{Cy} x_K^w & R_{32}^Y u_K^{Cy} y_K^w & R_{32}^Y u_K^{Cy} z_K^w & R_{33}^Y u_K^{Cy} x_K^w & R_{33}^Y u_K^{Cy} y_K^w & R_{33}^Y u_K^{Cy} z_K^w & R_{31}^Y u_K^{Cy} & R_{32}^Y u_K^{Cy} & R_{33}^Y u_K^{Cy} \\ R_{21}^Y x_K^w - & R_{21}^Y y_K^w - & R_{21}^Y z_K^w - & R_{22}^Y x_K^w - & R_{22}^Y y_K^w - & R_{22}^Y z_K^w - & R_{23}^Y x_K^w - & R_{23}^Y y_K^w - & R_{23}^Y z_K^w - & R_{21}^Y - & R_{22}^Y - & R_{23}^Y - \\ R_{31}^Y v_K^{Cy} x_K^w & R_{31}^Y v_K^{Cy} y_K^w & R_{31}^Y v_K^{Cy} z_K^w & R_{32}^Y v_K^{Cy} x_K^w & R_{32}^Y v_K^{Cy} y_K^w & R_{32}^Y v_K^{Cy} z_K^w & R_{33}^Y v_K^{Cy} x_K^w & R_{33}^Y v_K^{Cy} y_K^w & R_{33}^Y v_K^{Cy} z_K^w & R_{31}^Y v_K^{Cy} & R_{32}^Y v_K^{Cy} & R_{33}^Y v_K^{Cy} \\ \cdots & & & & & & & & & & & \cdots \end{bmatrix} \begin{bmatrix} R_{11} \\ R_{12} \\ R_{13} \\ R_{21} \\ R_{22} \\ R_{23} \\ R_{31} \\ R_{32} \\ R_{33} \\ t_1 \\ t_2 \\ t_3 \end{bmatrix} = 0$$

FIG. 6B

APPARATUS AND METHOD FOR WIDE-RANGE OPTICAL TRACKING DURING MEDICAL IMAGING

CROSS REFERENCE TO RELATED APPLICATIONS

This application claims the benefit of U.S. provisional patent application 62/505,751, filed on May 12, 2017, and hereby incorporated by reference in its entirety.

GOVERNMENT SPONSORSHIP

This invention was made with Government support under contract EB011654 awarded by the National Institutes of Health. The Government has certain rights in the invention.

FIELD OF THE INVENTION

This invention relates to medical imaging. More specifically, it involves the measurement of motion information from a human or animal subject during a medical imaging examination.

BACKGROUND

Motion remains a major problem in magnetic resonance imaging (MRI) of human and animal subjects. Motion of the imaged object relative to the magnetic fields used for spatial encoding leads to inconsistencies in the acquired data. When the data are transformed into an image, these inconsistencies result in 'motion artifacts', which can severely degrade image quality.

Neuroimaging forms a large part of clinical MRI examinations. This is due in part to the excellent soft-tissue contrast obtained, which is of particular value when examining brain tissue. A typical clinical neuroimaging exam requires the patient to hold their head in a fixed position with motion of less than a millimeter for several minutes at a time. An entire exam can take up to an hour, or longer, during which the subject is not supposed to move. This requirement is challenging even for healthy, collaborative subjects. In clinical situations, motion often occurs, particularly when imaging acute stroke patients, elderly patients with movement disorders, or pediatric patients. This can render images non-diagnostic, which in turn results in repeat scans. In many cases, particularly in pediatric imaging, the patient must be sedated prior to their scan. The end result is reduced diagnostic confidence, extra cost to the healthcare system, and inconvenience for the patient.

Motion of the head provides a somewhat simpler case than the motion of internal organs, or joints, since it can be approximated as rigid body motion. Rigid body motion neglects deformations and can be represented using six degrees of freedom: three translation parameters and three orientation parameters. Any combination of these translation and orientation parameters as applied to an object is referred to as the 'pose' of the object.

U.S. Pat. No. 5,545,993 (Taguchi and Kido, 1996) describes a method where the encoding fields in MRI are continuously updated during an exam to compensate for motion measured in six degrees of freedom. This is well suited for head motion, since the six degrees of freedom form a good approximation to the true motion, and they can be measured using one of several available methods. This technique is now well known in the MRI field and is often referred to as 'prospective motion correction' or 'adaptive motion correction'. For neuroimaging applications, a number of methods have been used to obtain the required head pose data: one such method is optical tracking, which typically uses a camera. Optical tracking has advantages over other techniques, as it is independent of the MRI system and can operate at relatively high temporal resolution.

U.S. Pat. No. 8,848,977 (Bammer, Forman, Aksoy, 2014) describes how the six degrees of freedom required to represent head motion can be obtained using a single camera and single, three-dimensional, marker. The marker includes a checkerboard pattern, where each square on the checkerboard contains a unique barcode that is used to match the corner points of the square to their position in a computer model of the marker. This method is particularly practical, since there is no requirement that the entire marker be visible for motion tracking. This has a major advantage over other techniques, because line of sight between the camera and marker is often partially obscured by the scanner head coil or the hair of the patient. Also, for setups where cameras are placed on or inside the head coil, it is common that part of the marker lies outside the field of view of the camera, due to the proximity of the camera to the patient's head.

We have previously demonstrated that motion correction using such a system performs well for most sequences in a clinical neuroimaging protocol (Aksoy et al., ISMRM 2014, Milan, Italy). In our experience, the system is effective for many, if not most, patients undergoing neuroimaging examinations with MRI. However, the same hardware is typically used for imaging all patients from neonates to adults. There is therefore a vast range in both expected head size and motion range of patients.

Accordingly, it would be an advance in the art to provide improved motion tracking in medical imaging systems.

SUMMARY

This work addresses the need described above, i.e., the ability to obtain object pose information over a wider range of positions than can be achieved using a single-camera, single-marker setup alone. While the present approach is particularly designed for tracking motion during MRI of human subjects, it will have application to other imaging modalities (such as CT and PET) or hybrid solutions (such as PET-CT and PET-MR), as well as for animal imaging.

In this work, we disclose how multiple cameras can be used together to dramatically expand tracking range. It is well known to those skilled in the art that multiple cameras can be used to track an object. The common use case for multiple cameras is stereovision, where two cameras are used to obtain two different views of the same object allowing depth information to be computed from the fact that two slightly different vantage points were used. Note that the present work differs substantially from stereovision approaches, as the data obtained by each camera individually is often sufficient to compute the pose of the marker, due to an inherent knowledge of the marker geometry.

In a preferred embodiment, two or more cameras are integrated into the head coil of the MRI scanner. The cameras are directed towards the marker, which is attached to a human subject. The cameras are separated slightly, so that their fields of view only partially overlap or do not overlap at all. This allows the combined field of view of all cameras together to be as large as possible. Note that this setup is unlike the stereo-vision scenario, where overlap between the field of views of each camera would be required for pose determination. In a preferred embodiment, the cameras are used to extend the tracking range in the longitudinal (head-feet) direction.

In a preferred embodiment, the marker used is a 'self-encoding' marker where a partial view of the marker is sufficient to calculate its pose (comprising three rotations and three translations). The marker includes 'feature points', where the relative location of each feature point is known. However, the methods described are also applicable to any marker that has the property that its pose can be determined from a single view. In another embodiment, each marker can be a three-dimensional constellation of reflective spheres, where the geometry of the marker is known and a single view of the marker is sufficient to calculate its pose. In another embodiment, each marker can use moiré patterns so that out-of-plane rotations are accurately quantifiable and a single view of the marker is sufficient to calculate its pose.

In a preferred embodiment, the marker is placed on the forehead of the subject. The positioning of the marker is such that the marker lies in the field of view of at least one of the cameras. Video data from the two or more cameras are transmitted from the scanner to an image processing apparatus. In addition, the cameras are synchronized, and the camera frames are time stamped, so that frames from each of the cameras can be matched.

In a preferred embodiment, the augmented discrete linear transform (DLT) algorithm described in the following is applied to compute the pose of the marker. The augmented DLT algorithm finds an optimal pose estimate of the self-encoding marker, based on the feature points visible to each of the cameras.

In a preferred embodiment, the pose of the marker is calculated for each temporal frame resulting in motion data, which is then used to adaptively update the MRI scanner in real-time to prevent motion artifacts.

In a preferred embodiment, the entire system is scalable from two cameras, up to n cameras, where n is sufficiently high to ensure robust motion tracking for all subjects over all realistic motion ranges.

In another embodiment, the cameras are not synchronized, but are time stamped so that the relative timing between any pair of camera frames from any of the cameras is known. Data are then combined taking the relative timing into consideration, for example by using a Kalman filter approach.

In another embodiment, the cameras are neither time stamped nor synchronized. Camera frames are sent asynchronously to the processing computer and the current knowledge of the object pose is updated using the most recent camera frame to arrive.

In another embodiment, the cameras are placed so as to improve the accuracy and precision of the pose determination along a particular direction.

In another embodiment each marker can be an anatomical feature, such as the nose, a mole or simply skin texture with unique structural features, which can be further enhanced by variable lighting conditions.

In another embodiment, camera data transmission is performed wirelessly, and extra cameras can be simply added or removed as required, without requiring the routing of fiber. This approach takes full advantage of the scalability of the data combination methods described in this work.

BRIEF DESCRIPTION OF THE DRAWINGS

FIG. 6B shows exemplary equations for solving for the pose of the marker using the augmented DLT algorithm.

DETAILED DESCRIPTION

A) General Principles

Figure 1A:
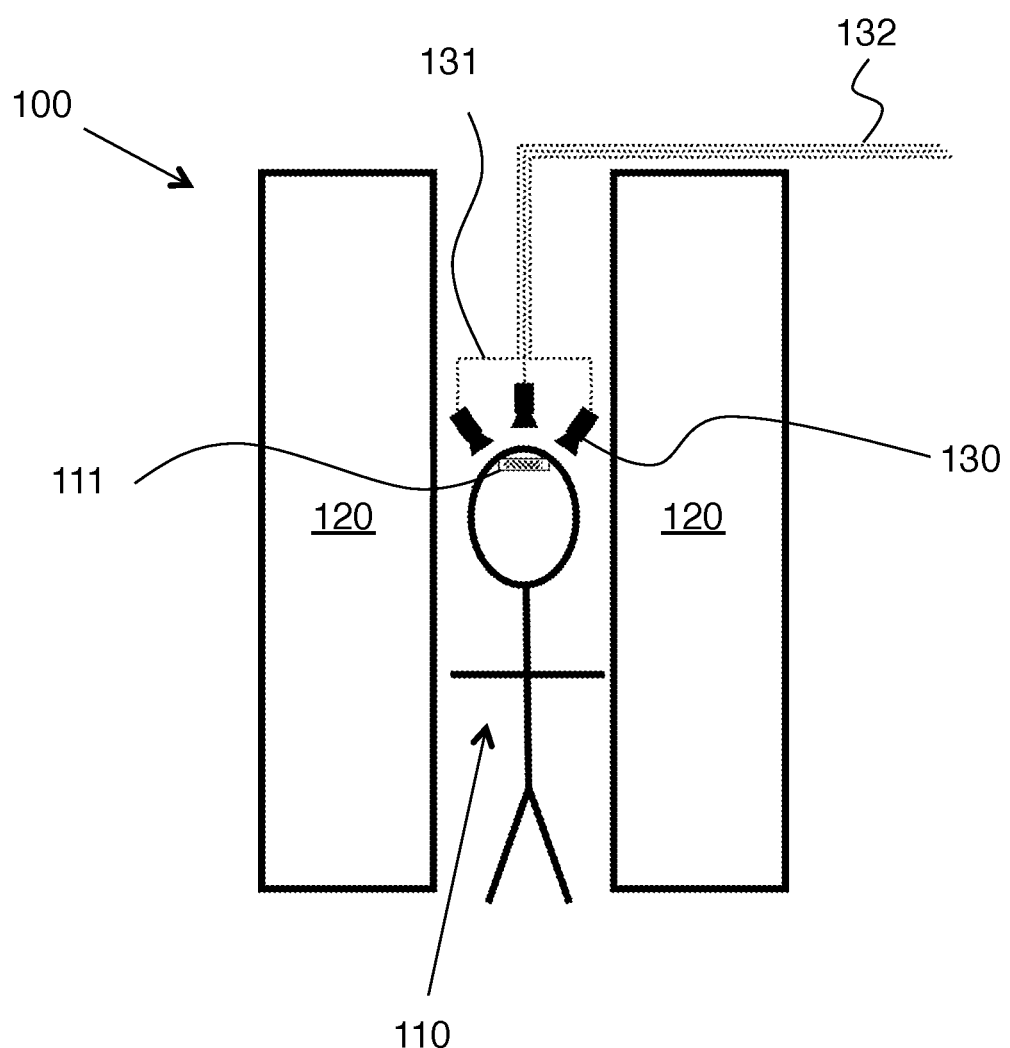
FIG. 1A shows a human subject with a marker attached rigidly to their head lying inside an MRI scanner, which includes three cameras that independently track the pose of the marker.

To better appreciate the present invention, it will be helpful to briefly describe some embodiments with reference to the subsequent description. An exemplary embodiment of the invention is a method of determining a position and orientation of an object in a medical imaging device. The method includes five main steps.

1) Providing one or more markers rigidly attached to the object, where each marker includes three or more feature points, and where the feature points of each marker have known positions in a coordinate system of the corresponding marker. In other words, the feature points are marker features that can be distinguished from each other in images and which have known relative positions with respect to each other, provided they are on the same marker.

2) Providing two or more cameras configured to have partial or full views of at least one of the markers.

3) Determining a camera calibration that provides transformation matrices $T_{ij}$ relating a coordinate system $C_i$ of camera i to a coordinate system $C_j$ of camera j. Here i and j are index integers for the two or more cameras. See Eqs. 1 and 3 below for examples of such transformation matrices.

4) Forming two or more images of the one or more markers with the two or more cameras. Here the known positions of the feature points of each marker in the coordinate systems of the corresponding markers lead to image consistency conditions for images of the feature points in the camera coordinate systems. See Eqs. 2 and 4 below for examples of such consistency conditions. Here image consistency conditions refer to relations that are true in images of the markers because of the known relative positions of feature points on each marker. As a simple example, suppose three feature points are equally spaced in the x-direction of the marker coordinate system. That equal spacing relation will lead to corresponding relations in images including these three feature points. This kind of consistency condition is a single-image consistency condition, and is different from image to image consistency checks performed to see if a marker has moved, as described below.

5) Solving the image consistency conditions to determine transformation matrices $M_k$ relating the coordinate systems $MC_k$ of each marker k to the coordinate systems of the cameras, wherein k is an index integer for the one or more markers, whereby position and orientation of the object is provided. See FIG. 6B for an example of a system of image consistency conditions.

The cameras are preferably compatible with magnetic fields of a magnetic resonance imaging system. The one or more markers can include a position self-encoded marker. The object can be a head of a human subject.

The camera calibration can be performed prior to installing the cameras in the medical imaging device. The camera calibration can include referencing each camera to system coordinates of the medical imaging device and enforcing consistency conditions for the camera calibration.

All or fewer than all visible feature points of the markers in the images can be used in the solution of the image consistency conditions. A frame capture timing of the two or more cameras can be offset to increase an effective rate of tracking. The cameras can be arranged to increase a marker tracking range in a head-feet direction of a patient being imaged.

The position and orientation of the object can be used to apply motion correction to medical imaging data. Such motion correction can be applied adaptively. In cases where two or more markers are attached to the object, analysis of the relative position of the two or more markers can be performed as a marker consistency check. If this marker consistency check fails, the motion correction can be disabled.

Solving the image consistency conditions can be performed with a least squares solution to an overdetermined system of linear equations (i.e., more equations than unknowns).

B) Examples

Figure 1B:
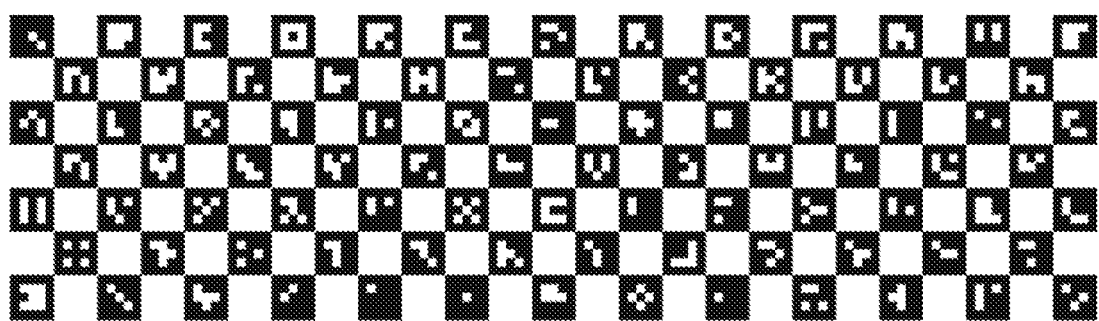
FIG. 1B shows an example of an optical tracking marker with a self-encoding pattern.

FIG. 1A shows an exemplary MRI system 100. A patient 110 is lying inside an MRI scanner 120. The patient wears an optical tracking marker 111 on their forehead. Several cameras 130 are positioned so as to have a view of the patient's forehead. Data from the cameras are transferred out of the scanner via optical fiber 131. Individual fibers can be combined together into a single fiber bundle 132 for easy handling. Alternatively, the cameras may be wireless, which has the advantage of complete flexibility in terms of the number of cameras used, since the system is highly modular and adding an extra camera does not affect the existing cameras. FIG. 1B shows an example of an optical tracking marker with a self-encoding pattern.

Figure 2A:
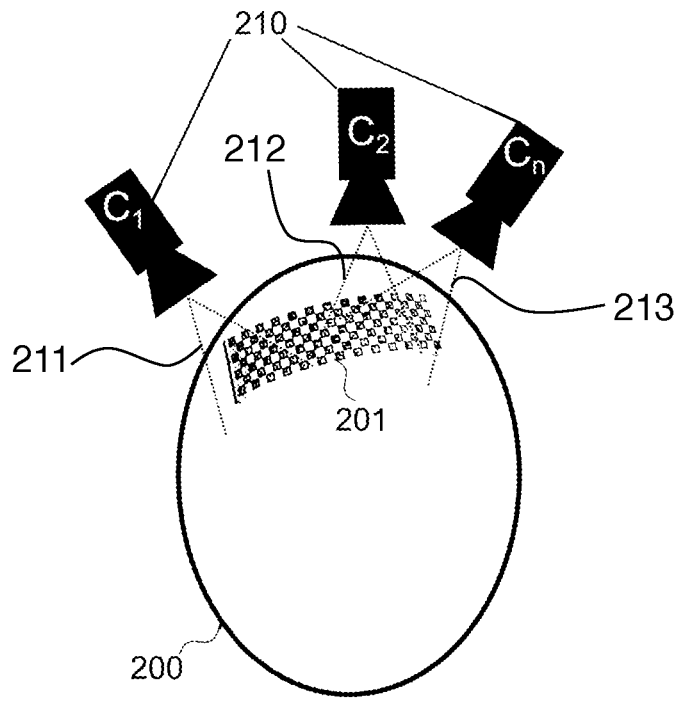
FIG. 2A shows n cameras positioned to view a marker placed on the forehead of a subject.

FIG. 2A shows the head of a human subject 200 with an attached marker 201. Two or more cameras 210 are positioned so as to have a view of the marker. Whether or not the field of view from each camera overlaps is of no consequence. In this example, the field of view 211 of Camera 1 does not overlap with that of any other camera. However, the field of view 212 of Camera 2 does overlap with the field of view 213 of Camera n. This flexibility is unlike conventional stereo vision approaches, which require a field of view with as much overlap as possible between the two cameras in order to calculate the object pose.

Figure 2B:
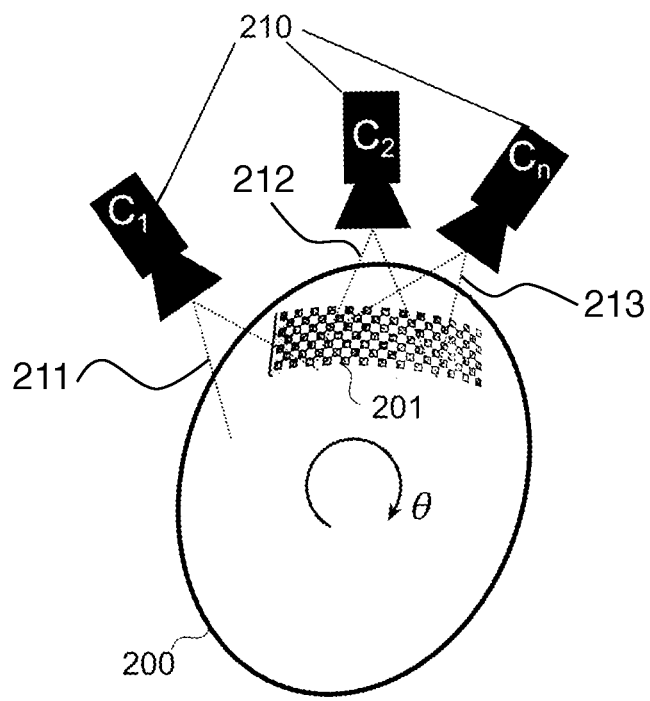
FIG. 2B shows how the setup in FIG. 2A is robust to head motion and how the usefulness of particular cameras may increase or decrease as motion occurs.

FIG. 2B shows the setup in FIG. 2A after a head rotation denoted by θ. Following the rotation of θ, Camera 1 no longer has a robust view of the marker. Using the algorithms described here, its contribution to the pose estimation process will be decreased. Conversely, other cameras may now have a better view of the marker: their contributions to pose estimation will be automatically increased.

Figure 3A:
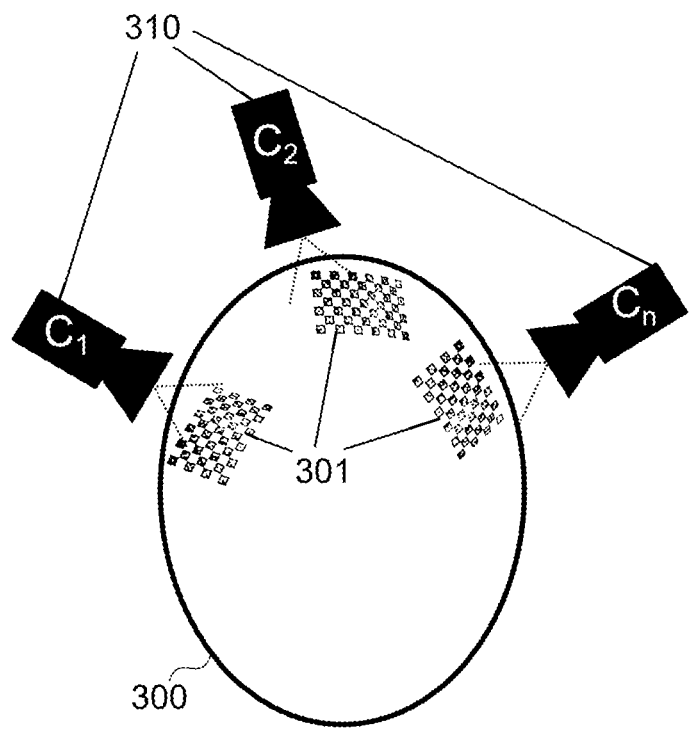
FIG. 3A shows how n cameras and n markers can be positioned to obtain tracking measurements from different locations on the surface of the head.
Figure 3B:
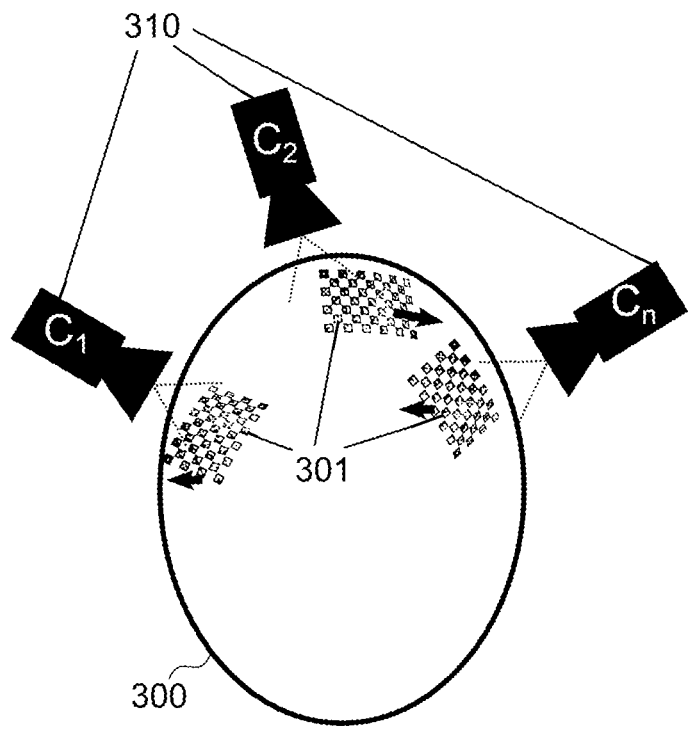
FIG. 3B shows how the setup in FIG. 3A can be used to detect inconsistent marker motion.

FIG. 3A shows an alternative implementation to FIGS. 2A-B, where multiple separate markers 301 are attached to the head of a human subject 300, rather than using a single marker, as shown in FIGS. 2A-B. Each marker is viewed by a separate camera 310 with non-overlapping fields of view. This implementation has advantages in the case of skin motion, which is typically a confounding non-rigid effect. Skin motion affects all markers differently, so there is an inherent averaging effect when the data are combined. FIG. 3B shows how the central marker could move differently than the left and right markers. When this happens, it is a strong indication that skin motion has occurred or that a marker has become dislodged and is no longer rigidly attached.

In the implementation shown in FIGS. 3A-B, the markers shown are self-encoding markers. However, any marker can be used that has the property that a full or partial view of it is sufficient to calculate its pose (comprising three translation parameters and three rotation parameters). There are many well-known markers that have this property, including rigid 3D constellations of reflective spheres or two-dimensional markers with integrated moiré patterns.

Figure 4A:
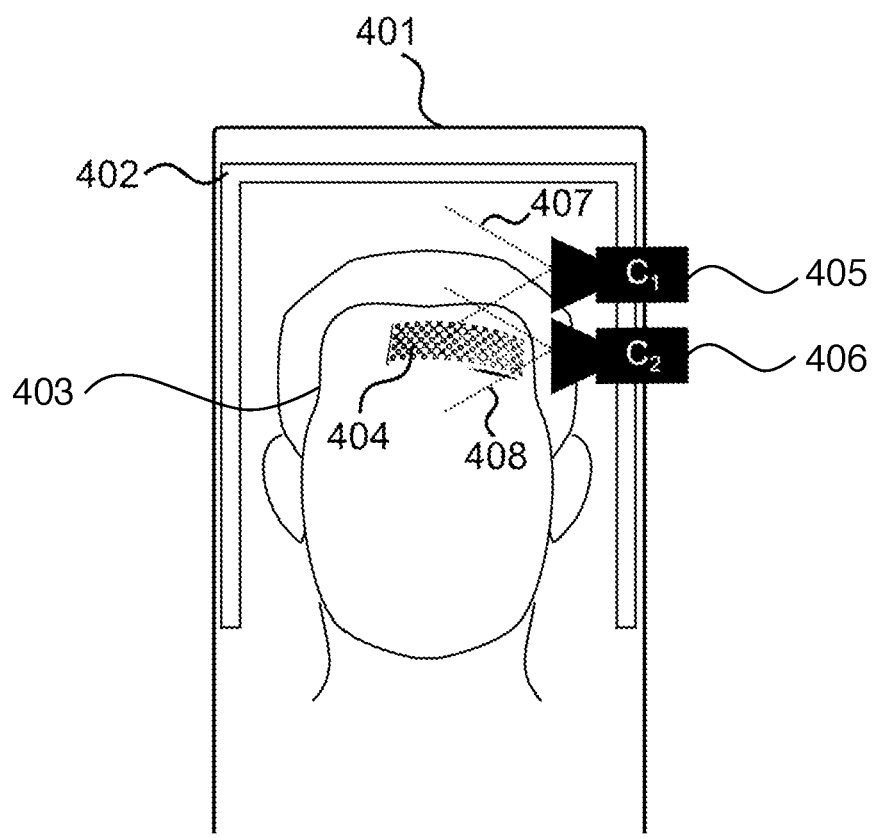
FIG. 4A shows how multiple cameras can be used to extend the effective field of view in the longitudinal (head-feet) direction.

FIG. 4A shows an arrangement that extends the tracking range of the optical system in the longitudinal (head-feet) direction. The patient table 401 is equipped with a head coil 402, where the subject's head 403 is positioned. A marker 404 is attached to the head of the subject. In practice, there is considerable variation in how far into the head coil the subject's head 403, and therefore the marker 404, lies. Two cameras (405 and 406) are placed on the head coil such that their fields of view (407 and 408) only partially overlap and so that the 'combined' field of view from both cameras covers a greater range in the head-feet direction than a single camera alone. In this example, two cameras are used; however, this arrangement is not limited to two cameras, and any number of extra cameras can be added depending on the desired tracking range.

Figure 4B:
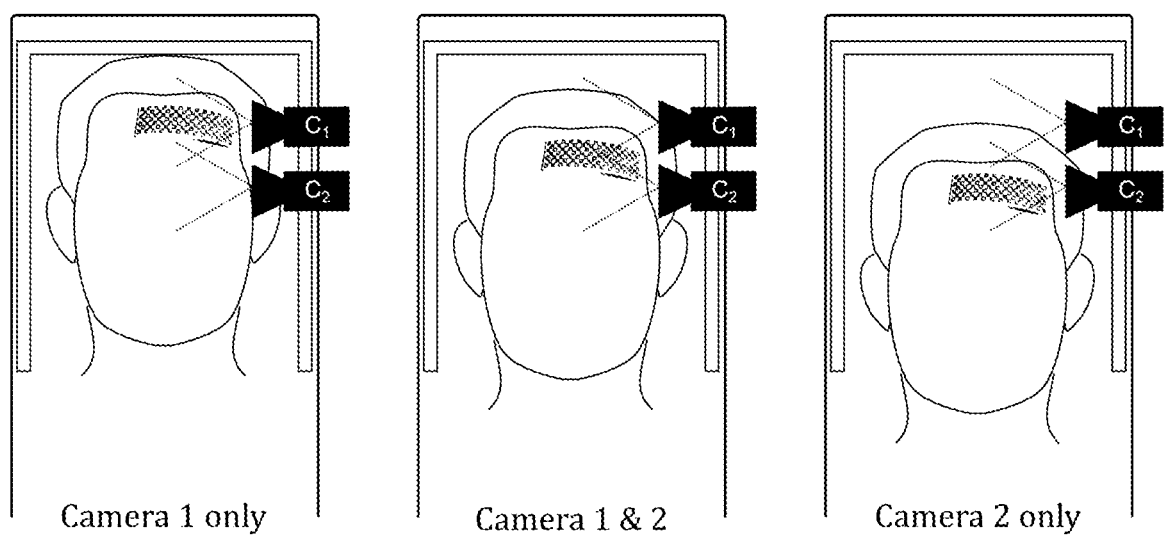
FIG. 4B shows how the setup in FIG. 4A allows a subject's head to be tracked at different positions in the head coil by using multiple cameras on their own or together.

FIG. 4B shows three modes of operation of the apparatus shown in FIG. 4A. The diagram on the left illustrates the situation where the subject's head is fully inserted into the head coil. In this case, the marker lies in the field of view of Camera 1, but not of Camera 2. No data combination is required, since tracking data from Camera 1 alone may be used. The diagram in the middle illustrates the situation when the subject's head is placed in a neutral position in the head coil. In this case, the marker lies in the field of view of both Camera 1 and Camera 2. Although data from either camera could be used alone, discarding the other, this would be sub-optimal, and data fusion as described below should instead be used. The diagram on the right illustrates the situation where the subject's head does not reach far into the head coil, which can occur in subjects with shorter necks. In this case, the marker lies in the field of view of Camera 2, but not in the field of view of Camera 1. Here data fusion is not required, since tracking data from Camera 2 alone may suffice. In our experience, subjects move sufficiently during their MRI examination that the marker can move from the field of one camera to the other. Therefore, data fusion is preferably always used, so that such patient motion is automatically handled.

Figure 5A:
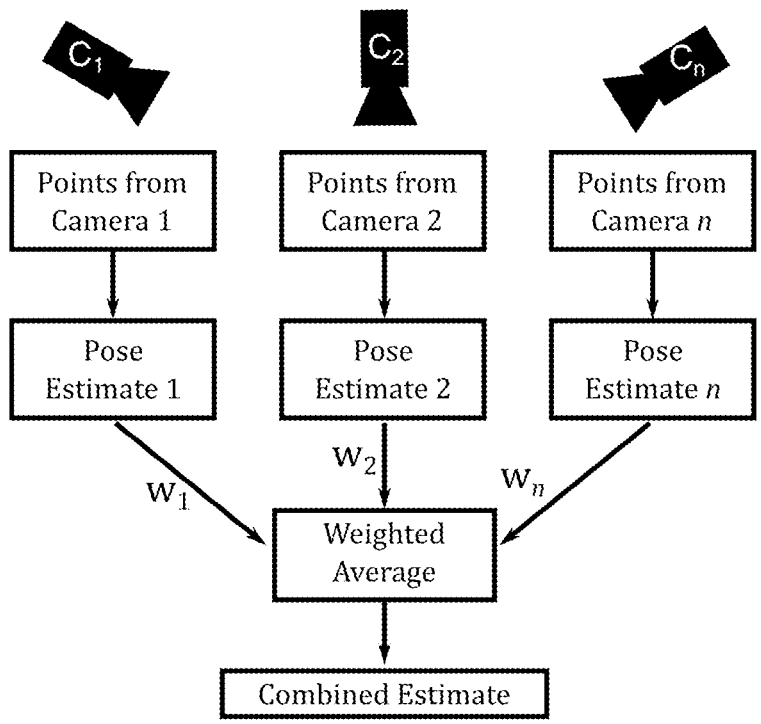
FIG. 5A shows how measurements obtained from video data from each camera can be combined to form a single estimate using the pose combination algorithm.
Figure 5B:
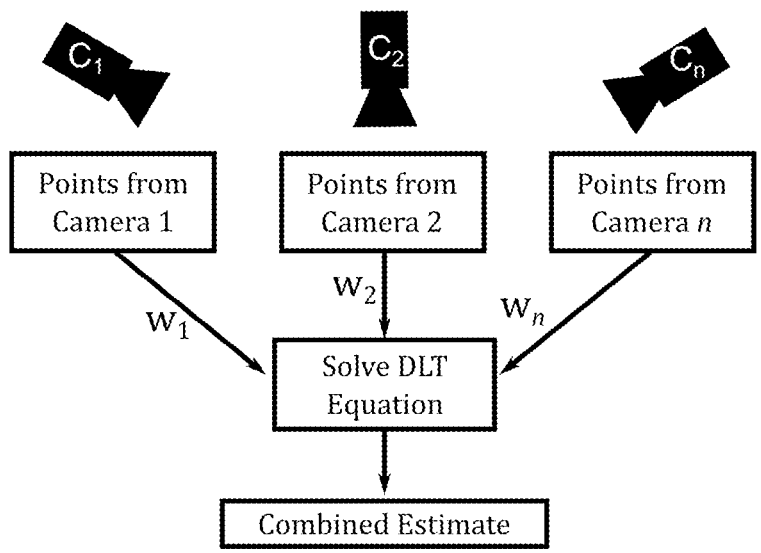
FIG. 5B shows how measurements obtained from video data from each camera can be combined to form a single estimate using the augmented DLT algorithm.

FIGS. 5A-B show two methods that can be used to combine pose measurements obtained from video data from each camera to form a single estimate. We refer to the two methods as (FIG. 5A) the 'pose combination algorithm' and (FIG. 5B) the 'augmented DLT algorithm', where DLT is an abbreviation for the well-known discrete linear transform. The augmented DLT algorithm is our preferred method for use with the self-encoded marker design described here. To better appreciate the preferred DLT approach, it is helpful to summarize the pose combination algorithm.

The pose combination algorithm (FIG. 5A) works as follows. At any point in time the latest pose is calculated from the latest frames from all cameras that observed the marker. Given n cameras, n individual pose estimates are computed and then one 'optimal' estimate is computed from these. For each individual pose estimate, a scalar weight, $w_i$, is computed, which represents the reliability of the estimate for camera i and where $$\sum_{i=1}^{n} w_i = 1.$$

The estimates are then combined using a weighted sum. For the translation component of pose, the combined estimate is given by $$t_c = w_1 t_1 + w_2 t_2 + \ldots + w_n t_n$$

where $t_i$, is the vector translation component of the pose estimate from camera i.

The combined estimate of the rotation component of each pose is computed using a similar weighting procedure. However, simply averaging rotation matrices or Euler angles is not a mathematically valid approach. Instead, rotations components derived from the individual camera views are first expressed as unit quaternions, $q_i$. Then the combined estimate is calculated as $q_c$, using one of several known methods, such as spherical linear interpolation (slerp) or the method of Markley, et al., "Averaging Quaternions", Journal of Guidance, Control and Dynamics, Vol. 30, No. 4, 2007. In our experience, when the unit quaternions to be averaged all represent a similar rotation, a simple and computationally efficient approximation to these methods can be obtained using the following procedure:
1) Changing the sign of all unit quaternions with negative real part (q and –q represent the same rotation, but can't be easily averaged).
2) Taking the mean of all n unit quaternions by adding all components and dividing by n.
3) Renormalizing by dividing the result from (2) by its norm, so that the combined quaternion, $q_c$, is a unit quaternion.
If weighted averaging is desired, then weights can be easily included as part of Step (2).

The augmented DLT algorithm (FIG. 5B) differs significantly from the pose combination algorithm and is a novel approach that we have developed to optimally combine camera data from a single self-encoded marker. Rather than computing a pose estimate for each camera and then combining poses, the feature points are combined first and then a single pose is computed. This has a number of advantages relating to data weighting, which is performed automatically by the algorithm, rather than requiring the specific calculation of weights. A common example is the situation with one marker and two cameras, where one of the cameras has a good view of the marker (>40 points), but the other camera has a poor view (<15 points). By combining the points prior to pose calculation, the camera with the best view automatically receives the higher weighting, since a greater number of points from that camera are being used to calculate the marker pose.

Figure 6A:
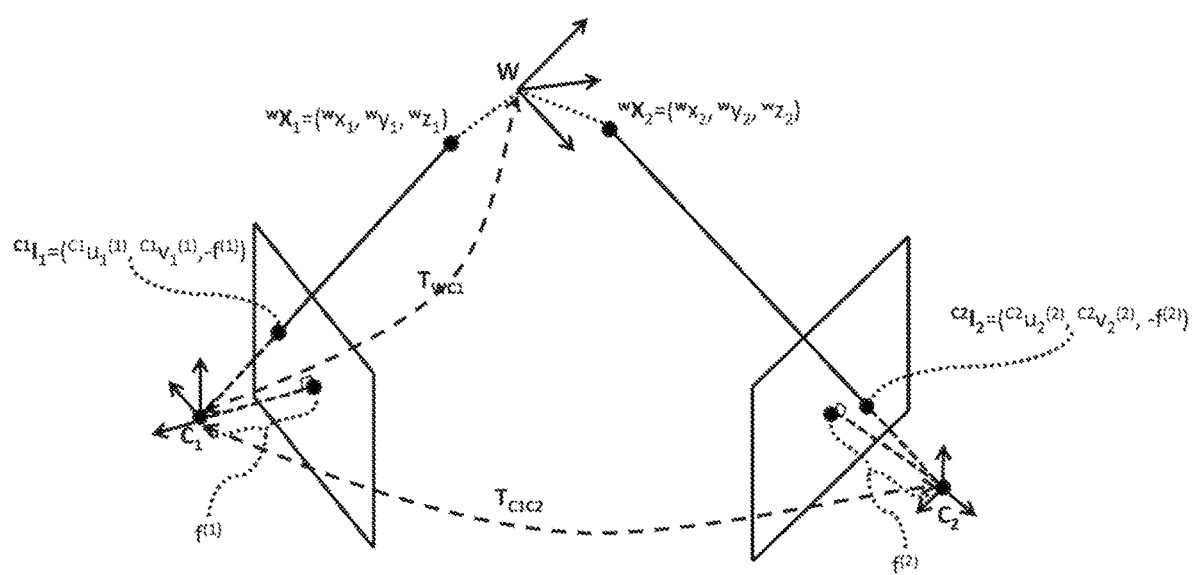
FIG. 6A shows how the augmented DLT algorithm finds the pose of the marker based on input from any number of cameras.

FIG. 6A further illustrates how the augmented DLT algorithm functions. In this example, there are two cameras, C1 and C2, but the same principles apply to any number of cameras. It is important to note that this augmented DLT algorithm is completely different than stereovision. In stereovision, a point cloud is extracted from the scene, such that all points in the cloud are visible to all cameras. Additionally, the relative locations of these points in the cloud are unknown. In contrast, in our case, a marker with known geometry is tracked, i.e., the locations of the points with respect to each other are known. Additionally, the tracked points need not be in the field-of-view of all cameras: different cameras can see different parts of the object and can still fuse the data to form a single pose estimate. This scenario is depicted in FIG. 6A where the two points $^{w}X_1$ and $^{w}X_2$ are visible to Cameras 1 and 2, respectively.

The augmented DLT algorithm determines the pose of the marker coordinate frame (W) with respect to a reference camera frame (arbitrarily chosen to be $C_1$ in this example). This pose is represented by a 4-by-4 transformation matrix $T_{WC1}$. Here, we are assuming that the extrinsic calibration of the camera system is already known, i.e., the transformation matrix $T_{C1C2}$ linking the two coordinate frames.

Cameras 1 and 2 track two points, $^{w}X_1$ and $^{w}X_2$, respectively. The left superscript w indicates that $^{w}X_1$ and $^{w}X_2$ are defined with respect to the coordinate frame W, i.e., $$^{C1}X_1 = T_{WC1} {}^{W}X_1$$

$$^{C2}X_1 = T_{C1C2} T_{WC1} {}^{W}X_1 \qquad (1)$$

In practice, the coordinate frame W corresponds to the coordinate frame defined by the marker.

Using the pinhole camera model, the projection of $^{C1}X_1 = (^{C1}x_1, {}^{C1}y_1, {}^{C1}z_1)$ on the first camera image plane) $^{C1}I_1 = (^{C1}u_1^{(1)}, {}^{C1}v_1^{(1)}, -f^{(1)})$ can be determined as:

$$^{C1}u_1^{(1)} = f^{(1)} \frac{^{C1}x_1}{^{C1}z_1} \qquad (2)$$

$$^{C1}v_1^{(1)} = f^{(1)} \frac{^{C1}y_1}{^{C1}z_1}$$

where $f^{(1)}$ is the focal length of camera 1. Note that in Eq. 2, we used the coordinates $^{C1}X_1$, but in fact one knows $^{w}X_1$. Another important point is that the coordinates u and v in Eq. 2 are still defined with respect to a physical coordinate system C1, and are represented in physical units (e.g., millimeters). However, in reality, the location of a projected point on a camera image is described in pixels. The conversion from detected camera image pixel coordinates to physical coordinates (u, v) involve other steps, such as re-centering depending on the offset between centers of the lens and detectors, and correcting for radial and tangential lens distortions. However, pixel-to-physical conversion rules are constant for a camera and can be determined offline using well-known intrinsic camera calibration methods (e.g., Zhang Z. A flexible new technique for camera calibration. IEEE Transactions on Pattern Analysis and Machine Intelligence 2000; 22:1330-1334. doi: 10.1109/34.888718). Thus, without loss of generality, it can be assumed that (u, v) coordinates in Eq. 2 can easily be determined from the pixel coordinates on the image. In fact, we can also drop the focal length $f^{(1)}$ in Eq. 2 by re-defining u' and v' such that u'=u/f and v'=v/f.

The transformation matrix between the marker and Camera 1, and between Camera 1 and Camera γ, can be defined as $$T_{WC1} = \begin{bmatrix} R_{11} & R_{12} & R_{13} & t_1 \\ R_{21} & R_{22} & R_{23} & t_2 \\ R_{31} & R_{32} & R_{33} & t_3 \\ 0 & 0 & 0 & 1 \end{bmatrix} \quad (3)$$

$$T_{C1C\gamma} = \begin{bmatrix} R_{11}^{\gamma} & R_{12}^{\gamma} & R_{13}^{\gamma} & t_1^{\gamma} \\ R_{21}^{\gamma} & R_{22}^{\gamma} & R_{23}^{\gamma} & t_2^{\gamma} \\ R_{31}^{\gamma} & R_{32}^{\gamma} & R_{33}^{\gamma} & t_3^{\gamma} \\ 0 & 0 & 0 & 1 \end{bmatrix}$$

where γ is the camera index. In both cases, the 3-by-3 matrix R represents the rotation and the 3-by-1 vector t represents translation. $T_{C1C\gamma}$ is already known through extrinsic camera calibration and $T_{WC1}$ is the marker pose that is to be determined using DLT. Assuming arbitrary point κ and camera γ, we can re-arrange Eq. 2 to get (and dropping the focal length):

$$^{C\gamma}u_\kappa(\gamma)^{C\gamma}\tilde{z}_\kappa - {}^{C\gamma}x_\kappa = 0$$

$$^{C\gamma}v_\kappa(\gamma)^{C\gamma}\tilde{z}_\kappa - {}^{C\gamma}y_\kappa = 0 \quad (4)$$

Combining Eqs. 1, 3, 4 and cascading the equations for each detected point for all cameras gives a system of equations as shown on FIG. 6B. On this figure a condensed notation is used where coordinate systems are indicated with a right superscript instead of with a left superscript. Another notation change here is that the explicit notation of right superscript to denote the camera is dropped because the coordinate system being used suffices to identify the corresponding camera. FIG. 6B shows two equations for a single feature point as seen by one camera. The expressions for the matrix elements are given on two lines to make the expression compact enough to fit on the page. Such pairs of equations will exist for each feature point on the marker that is seen by each camera.

More explicitly, the matrix in FIG. 6B is $$\sum_{\gamma=1}^{n_\gamma} n_k^{(\gamma)}$$

-by-12, where $n_\gamma$ is the total number of cameras and $n_n^{(\gamma)}$ is the number of points detected by camera γ. In cases where more than one marker is employed, a system of equations as in FIG. 6B can be solved for each marker.

Solution of the system of FIG. 6B and extraction of rotation and translation parameters is straightforward using singular value decomposition or iterative methods (Hartley R, Zisserman A. Multiple View Geometry in Computer Vision. 2003.).

Figure 7:
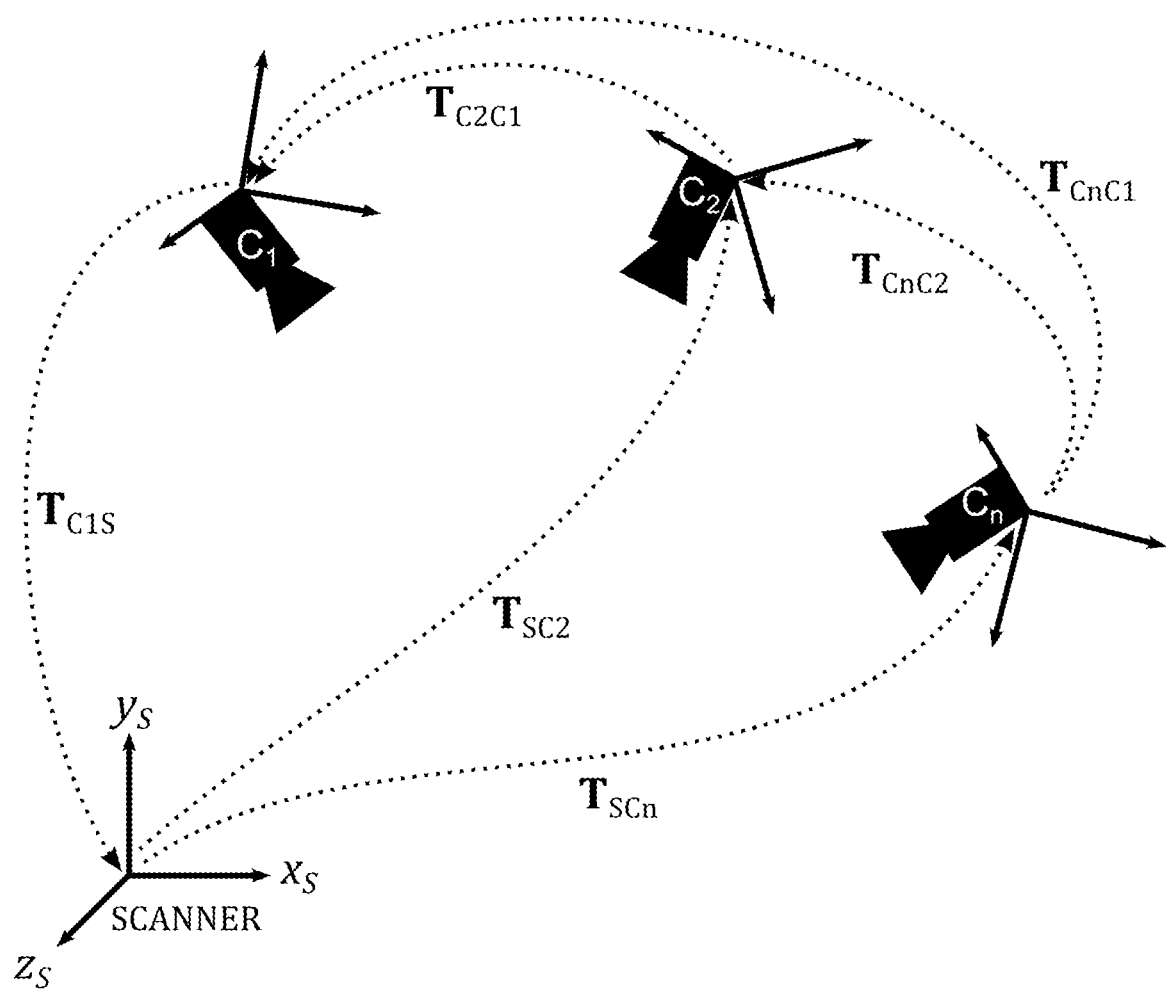
FIG. 7 shows how homogeneous transformations can be used to relate the coordinate frames between the MRI scanner and any number of cameras.

FIG. 7 shows how the coordinate frames between the MRI scanner and two cameras, Camera 1 and Camera 2, are connected using homogeneous transformations. The knowledge of these transformations is needed for the methods described in this work. The means of obtaining the transformation between two cameras is well known to those in the field, as is the means to obtain the calibration between a single camera and the MRI scanner. However, due to the use of multiple cameras, it is possible to optimize these transformations to enforce consistency. Assuming the total number of cameras is two, then there are three relevant transformations, namely $T_{C1S}$ (linking Camera 1 and the scanner), $T_{C2C1}$ (linking Camera 1 and Camera 2) and $T_{SC2}$ (linking Camera 2 and the scanner). As seen in FIG. 7, if these transformations are correct and are applied sequentially, then an identity transform results, i.e., $$T_{C1S}T_{C2C1}T_{SC2} = I \quad (5)$$

Well-known iterative optimization methods can be used to modify the measured transformations, such that the above equation holds, and while satisfying constraints such as
1) Even distribution of errors between scanner-camera cross-calibration transformations $T_{C1S}$ and $T_{C2C1}$ and/or
2) No errors in $T_{C2C1}$ because camera-camera calibration can be done to far greater accuracy than scanner-camera calibration.

Given more than two cameras, it is possible to formulate the optimal solution of scanner-camera transformation in a least squared sense as follows. Arbitrarily choosing C1 as the reference frame, one can obtain:

$$\tilde{T}_{C1S} \approx T_{C1S} \quad (6)$$

$$\tilde{T}_{C2S} \approx T_{C1S}T_{C2C1}$$

$$\vdots$$

$$\tilde{T}_{C\gamma S} \approx T_{C1S}T_{C\gamma C1}$$

Here, $\tilde{T}_{C1S}$, $\tilde{T}_{C2S}$ and $\tilde{T}_{C\gamma S}$, are the measured camera-to-scanner transformations for cameras 1, 2 and γ. As mentioned above, the transformation between camera and MRI scanner can be obtained using methods well known to those in the field. In addition, the camera-to-scanner transformations for all cameras can be obtained within one experiment without additional time overhead. In Eq. 6, $T_{C\gamma C1}$ represents the transformations between camera γ and camera 1, and can be obtained outside the MRI scanner with a high degree of accuracy. $T_{C1S}$ in Eq. 6 is the reference-camera-to-scanner transformation that needs to be determined from the equations. Re-writing Eq. 6 as a least-squares problem:

$$T_{C1S} = \underset{T'_{C1S}}{\mathrm{argmin}} \left\{ \sum_{\gamma=1}^{n_\gamma} \left\| \tilde{T}_{C\gamma S} - T'_{C1S} T_{C\gamma C1} \right\|^2 \right\} \quad (7)$$

Eq. 7 represents a linear-least-squares problem with respect to the variables in $T_{C1S}$, so it can be solved using any available linear equation solver. It is also possible to solve Eq. 7 using non-linear methods, such as Levenberg-Marquardt or Gauss-Newton. One can also solve Eq. 7 by separating the rotational and translational components and solving for the rotational component of the transformation matrices first.

Figure 8:
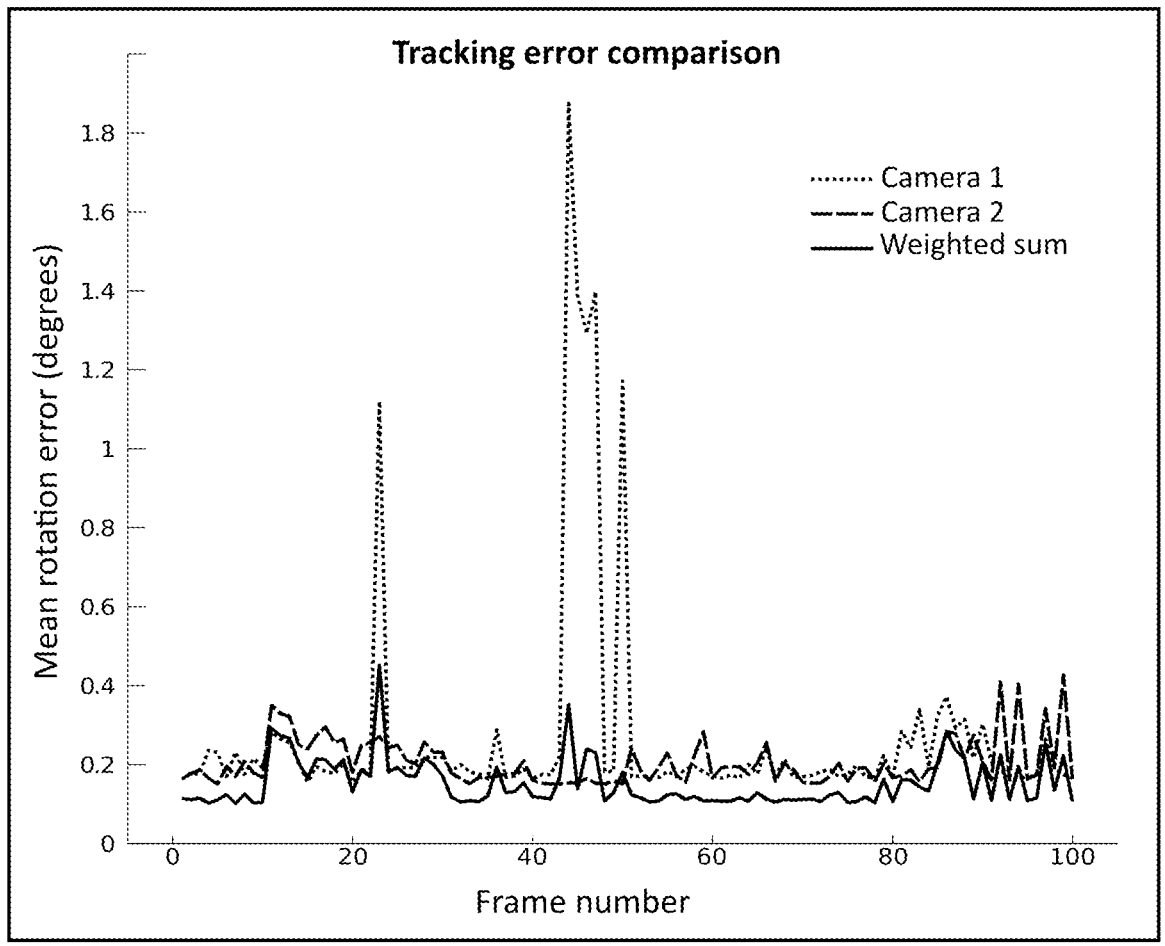
FIG. 8 provides experimental results showing that the mean rotation error can be improved by combining data from two cameras using the pose combination algorithm.

FIG. 8 shows experimental results obtained from an implementation of the pose combination algorithm shown in FIG. 5A. In this experiment, a rotation stage was used to give ground truth information. A marker was moved while video data were collected using two cameras. The graph shows a comparison of errors in rotation for each camera individually and for the combined estimate (labeled 'Weighted sum'). Of note is the spike in rotation error for Camera 1 between frames 40 and 50. This was caused by a poor view of the marker, leading to an ill-conditioned problem and noise in the pose estimate. Fortunately, in such event the weighted sum approach substantially reduces the rotation estimate error. Similar automatic and adaptive compensation for poor views from individual cameras can be obtained from the augmented DLT method of FIG. 5B.

The invention claimed is:

1. A method of determining a position and orientation of an object in a medical imaging device, the method comprising:

rigidly attaching one one or more markers to the object, wherein each marker of the one or more markers comprises three or more feature points, wherein the three or more feature points of each marker of the one or more markers have known positions in a coordinate system of the corresponding marker;

configuring two or more cameras to have partial or full views of at least one of the one or more markers;

determining a camera calibration that provides transformation matrices $T_{ij}$ relating a coordinate system $C_i$ of camera i to a coordinate system $C_j$ of camera j, wherein i and j are index integers for the two or more cameras;

forming two or more images of the one or more markers with the two or more cameras, wherein the known positions of the three or more feature points of each marker in the coordinate systems of the corresponding markers lead to image consistency conditions for images of the three or more feature points in the camera coordinate systems;

wherein the image consistency conditions are relations that are true in images of the one or more markers because of known relative positions of the three or more feature points on each of the one or more markers; and solving the image consistency conditions to determine rigid-body transformation matrices $M_k$ relating coordinate systems $MC_k$ of each marker k to the coordinate systems of the two or more cameras, wherein k is an index integer for the one or more markers, whereby the position and orientation of the object is provided;

wherein the solving the image consistency conditions to determine each rigid-body transformation matrix $M_k$ is performed with a least squares solution to an overdetermined system of linear equations;

wherein the overdetermined system of linear equations for rigid-body transformation matrix $M_k$ is a set of two equations for each feature point of marker k that is seen by each of the two or more cameras; and wherein the overdetermined system of linear equations for rigid-body transformation matrix $M_k$ has coefficients of the rigid-body transformation matrix $M_k$ as unknowns to be solved for.

2. The method of claim 1, wherein the two or more cameras are compatible with magnetic fields of a magnetic resonance imaging system.

3. The method of claim 1, wherein the one or more markers include a position self-encoded marker.

4. The method of claim 1, wherein the object is a head of a human subject.

5. The method of claim 1, wherein the camera calibration is determined prior to installing the two or more cameras in the medical imaging device.

6. The method of claim 1, wherein the camera calibration includes referencing each camera to system coordinates of the medical imaging device and enforcing consistency conditions for the camera calibration.

7. The method of claim 1, wherein all visible feature points of the one or more markers in the images are used in the solving of the image consistency conditions.

8. The method of claim 1, wherein fewer than all visible feature points of the one or more markers in the images are used in the solving of the image consistency conditions.

9. The method of claim 1, wherein a frame capture timing of the two or more cameras is offset, whereby an effective rate of tracking can be increased.

10. The method of claim 1, wherein the two or more cameras are arranged to allow a marker tracking range in a head-feet direction of a patient being imaged.

11. The method of claim 1, further comprising applying motion correction to medical imaging data based on the position and orientation of the object.

12. The method of claim 11, wherein the motion correction is applied adaptively.

13. The method of claim 12, wherein two or more of the one or more markers are attached to the object, and further comprising performing analysis of a relative position of the two or more markers as a marker consistency check.

* * * * *